(12) United States Patent
Noritake et al.

(10) Patent No.: US 7,667,194 B2
(45) Date of Patent: Feb. 23, 2010

(54) METHOD OF PRODUCING MICROARRAY

(75) Inventors: Motoo Noritake, Ichinomiya (JP);
Takao Ohnishi, Nishikasugai-Gun (JP);
Toshikazu Hirota, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 285 days.

(21) Appl. No.: 11/566,351

(22) Filed: Dec. 4, 2006

(65) Prior Publication Data

US 2007/0084997 A1    Apr. 19, 2007

Related U.S. Application Data

(63) Continuation of application No. PCT/JP2005/006816, filed on Mar. 31, 2005.

(30) Foreign Application Priority Data

Jun. 11, 2004    (JP) .............................. 2004-173417

(51) Int. Cl.
*H01J 49/00*    (2006.01)
*C12Q 1/68*    (2006.01)
(52) U.S. Cl. .................... 250/284; 250/288; 250/281; 250/282; 422/100
(58) Field of Classification Search .................... None
See application file for complete search history.

(56) References Cited

U.S. PATENT DOCUMENTS 6,089,693 A    7/2000    Drake et al.
6,731,781 B1 *   5/2004    Shams et al. ................. 382/129
6,734,424 B2 *   5/2004    Lennon et al. ............... 250/288
7,019,288 B2 *   3/2006    Becker ........................ 250/288
7,095,018 B2 *   8/2006    Barnes et al. ................ 250/288
7,160,512 B2     1/2007    Hirota et al.
7,294,831 B2 *  11/2007    Brown et al. ................. 250/288
7,361,311 B2 *   4/2008    Cooks et al. ................. 422/100
7,381,373 B2 *   6/2008    Blake et al. .................. 422/100
2003/0012698 A1 * 1/2003   Hirota et al. ................. 422/100
2003/0143329 A1   7/2003   Shchegrova et al.
2003/0143756 A1   7/2003   Fisher et al.

FOREIGN PATENT DOCUMENTS

EP    1 208 912 A1    5/2002
EP    1 254 704 A1    11/2002
GB    2 385 850 A1    9/2003
WO    02/090984       11/2002

* cited by examiner

*Primary Examiner*—David A. Vanore
(74) *Attorney, Agent, or Firm*—Burr & Brown

(57) ABSTRACT

A method of producing a microarray including: (A) ejecting a liquid sample from an outlet onto an inspection carrier to form inspection spots, inspecting the resultant inspection spots for their quality to determine whether the inspected spots are defective or successful, and detecting a defective discharge unit, if any; (B) making the detected defective discharge unit stop discharging the liquid sample to prevent formation of the defective sample spot; (C) forming successful sample spots on a carrier using successful discharge units to provide a successful microarray on which the successful spots are aligned in a predetermined pattern on the carrier; and (D) forming a successful spot to be formed originally on the successful microarray at the position of the defective spot where no spot is formed in step (B).

17 Claims, 5 Drawing Sheets

METHOD OF PRODUCING MICROARRAY

TECHNICAL FIELD

The present invention relates to a method of producing a microarray, including biochips and the like. More particularly, the present invention relates to a method of producing a microarray having spots that are formed stably with high precision and high density and having fewer defective spots that is used for high-definition, high-speed analysis. Such a microarray is produced by ejecting drops of a small volume of liquid sample onto a predetermined carrier or base to form small sample spots aligned and immobilized with high density on the carrier or the base.

BACKGROUND ART

Analysis of a gene structure has progressed remarkably in recent years. A number of gene structures including human genes have been revealed. For the analysis of a gene structure, a DNA microarray including biochips is used, where a solution containing thousands to millions of different DNA strands are aligned and immobilized as microspots on a carrier or a base such as a slide glass.

Such a microarray has been produced using an ink-jetting method in view of its high speed spot-formation action and uniform spot quality.

PCT International Patent Publication No. 02/90984 discloses a method of producing a biochip including a plurality of spots containing a plurality of liquid samples arranged with high density. This method includes the steps of providing a discharge unit comprising a body or a substrate and a piezoelectric/electrostrictive element; the body including an inlet, a channel, a cavity or a reservoir, and an outlet; introducing a liquid sample into the cavity through the inlet; disposing the carrier or the base at a position opposing the outlet; discharging the liquid sample introduced into the cavity from the outlet as small volume liquid drops to form a spot on the carrier or the base; and repeating the above steps for a plurality of liquid samples. According to this method, when using the discharge head including one or more discharge modules having one or more discharge units, at least one of a plurality of liquid samples is introduced into the cavity through the inlet of the discharge unit so that one liquid sample is provided in one discharge unit respectively. One or more trays on which one or more carriers or bases are fixed are removably mounted on a table and moved thereon to a discharge position of the discharge unit corresponding to a predetermined position of the carrier or the base. Each liquid sample introduced into the cavity is discharged to the predetermined position of the carrier or the base as liquid drops to arrange spots containing a plurality of liquid samples on the carrier or the base with high density. This method provides the advantage that the spots are formed with high definition in a short time.

DISCLOSURE OF INVENTION

At present, there are strong demands for high-quality microarrays. However, in the conventional production method, if any defective spots are formed during manufacturing, the apparatus producing the spots should be stopped, discharge conditions of the defective discharge unit from which the defective spots are produced should be reset, and/or liquid samples should be reintroduced into the discharge unit. Then, the apparatus is restarted using all dischargeable units including the restored defective discharge unit to restart the spot formation. In these methods, the production of the defective spots during recovery causes a problem. It is believed that one of the causes of defective spots is poor conditions of the discharge. The liquid sample within the discharge unit becomes precipitated or separated and the concentration thereof is changed resulting from a long downtime of the discharge unit; the liquid sample becomes dried and concentrated and a solid component is deposited near a discharge hole or a nozzle of the discharge unit; the discharge conditions become defective since the residence time of each liquid sample differs in each discharge unit; and so on. In addition, the determination of the defective discharge unit from which the defective spots are produced requires much time and effort, thereby decreasing the working efficiency. The present invention is made to solve the above-mentioned problems. An object of the present invention is to provide a method of producing a microarray having spots that are formed stably with high precision and high density and having fewer defective spots that is used for high-definition, high-speed analysis.

In order to achieve the object, the present invention provides a method of producing a microarray as follows:

[1] A first aspect of the present invention provides a method of producing a microarray including sample spots on a carrier in a predetermined pattern by providing a plurality of discharge units each including a substrate having an inlet, a channel, a reservoir, and an outlet of a liquid sample, and a piezoelectric/electrostrictive element disposed at a position corresponding to the reservoir on the substrate; and by ejecting a liquid sample discharged from the outlet to outside onto the carrier to form the sample spots corresponding to each discharge unit on the carrier, the method comprising the steps of: (A) ejecting the liquid sample discharged from the outlet to outside onto an inspection carrier to form inspection spots, inspecting the resultant inspection spots for their quality to determine whether the inspected spots are defective or successful, and detecting the defective discharge unit; (B) making the detected defective discharge unit stop discharging the liquid sample from the outlet to outside, to prevent the formation of a defective sample spot from the defective discharge unit; (C) forming successful sample spots on the carrier using successful discharge units excluding the defective discharge units to provide a successful microarray on which the successful spots are aligned in a predetermined pattern on the carrier; and (D) forming a successful spot to be formed originally on the successful microarray at the position of the defective spot where no spot is formed in step (B), thereby providing a finished microarray including the successful spots aligned on the carrier in a predetermined pattern.

[2] A method of producing a microarray according to [1], wherein a series of steps (A), (B) and (C) is repeated a plurality of times, and then step (D) is conducted.

[3] A method of producing a microarray according to [1] or [2], wherein the formation of the defective spot is stopped in step (B) by completely drawing out the liquid sample injected into the defective discharge unit.

[4] A method of producing a microarray according to [3], wherein the defective discharge unit is further cleaned after the liquid sample is drawn out.

[5] A method of producing a microarray according to [1] or [2], wherein the formation of the defective spot is stopped in step (B) by stopping the transmittance of an electrical signal for driving the piezoelectric/electrostrictive element.

[6] A method of producing a microarray according to any one of [1] to [5], wherein the distance between the inspection carrier and the outlet when the inspection spots are formed in step (A) be set to be greater than the distance between the carrier and the outlet when the successful spots are formed in step (C).

[7] A method of producing a microarray according to any one of [2] to [6], wherein when a plurality of successful microarrays are formed, the successful spot to be formed originally is formed in step (D) in a reverse order in step (C) on the successful microarray at the position of the defective spot where no spot is formed in step (B).

[8] A second aspect of the present invention provides a method of producing a microarray including sample spots on a carrier in a predetermined pattern by providing a plurality of discharge units each including a substrate having an inlet, a channel, a reservoir, and an outlet of a liquid sample, and a piezoelectric/electrostrictive element disposed at a position corresponding to the reservoir on the substrate; and by ejecting a liquid sample discharged from the outlet to outside onto the carrier to form the sample spots corresponding to each discharge unit on the carrier, the method comprising the steps of: (A) ejecting the liquid sample discharged from the outlet to outside onto an inspection carrier to form inspection spots, inspecting the resultant inspection spots for their quality to determine whether the inspected spots are defective or successful, and detecting a defective discharge unit; (B) making the detected defective discharge unit stop discharging the liquid sample from the outlet to outside, to prevent the formation of the defective sample spots from the defective discharge unit; (C) forming successful sample spots on the carrier using successful discharge units excluding defective discharge units to provide a successful microarray on which the successful spots are aligned in a predetermined pattern on the carrier; (E) inspecting the quality of the successful spot of the resultant successful microarray to detect a second defective discharge unit; (F) making the detected second defective discharge unit stop discharging the liquid sample from the outlet to outside, to prevent formation of a second defective sample spot from the second defective discharge unit; (G) forming second successful sample spots on the carrier using second successful discharge units excluding the defective discharge units and the second defective discharge units to provide a second successful microarray on which the second successful spots are aligned in a predetermined pattern on the carrier; and (H) forming a successful spot and a second successful spot, both to be formed originally, are formed on the second successful microarray at the position of the defective spot and the second defective spot where no spots are formed in steps (B) and (E), thereby providing a finished microarray including the successful spots and the second successful spots aligned on the carrier in a predetermined pattern.

[9] A method of producing a microarray according to [8], wherein a series of steps (A), (B), (C), (E), (F) and (G) is repeated a plurality of times, and then step (H) is conducted.

[10] A method of producing a microarray according to [8] or [9], wherein the quality of the successful spots on the resultant successful microarray is preferably inspected with image processing or human eye using a display means capable of displaying in a noticeable manner only the successful spots formed simultaneously in step (E), and is determined whether they are defective or successful, thereby to detect a second defective discharge unit.

[11] A method of producing a microarray according to any one of [8] to [10], wherein the formation of the defective spot and/or the second defective spot corresponding to the defective discharge unit and/or the second defective discharge unit is stopped in step (B) and/or (F) preferably by completely drawing out the liquid sample injected into the defective discharge unit and/or the second defective discharge unit.

[12] A method of producing a microarray according to [11], wherein the defective discharge unit and/or the second defective discharge unit are further cleaned after the liquid sample is drawn out.

[13] A method of producing a microarray according to any one of [8] to [10], wherein the formation of the defective spot and/or the second defective spot corresponding to the defective discharge unit and/or the second defective discharge unit is stopped in step (B) and/or (F) by stopping the transmittance of an electrical signal for driving the piezoelectric/electrostrictive element.

[14] A method of producing a microarray according to any one of [8] to [13], wherein the distance between the inspection carrier and the outlet when the inspection spots are formed in step (A) be set to be greater than the distance between the carrier and the outlet when the first and/or second successful spots are formed in steps (C) and/or (G)

[15] A method of producing a microarray according to any one of [8] to [14], wherein a successful spot and a second successful spot, both to be formed originally, are formed on the second successful microarray in step (H) at the position of the defective spot where no spot was formed in steps (B) and/or (F) in the reverse order of step (G).

[16] A third aspect of the present invention provides a microarray produced by using the method according to any one of [1] to [15].

According to the present invention, there can be provided a microarray having spots that are formed stably with high precision and high density and having decreased defective spots that is used for high-definition, high-speed analysis, when the microarray is produced by ejecting drops of a small volume liquid sample onto a predetermined carrier or support to form small sample spots aligned and immobilized with high density on a carrier or a base.

BRIEF DESCRIPTION OF THE DRAWINGS

FIG. 3(*a*) shows step (A), FIG. 3(*b*) shows steps (B) and (C), and FIG. 3(*c*) shows step (D).

FIG. 4(*a*) shows step (A), FIG. 4(*b*) shows steps (B) and (C), FIG. 4(*c*) shows step (E), FIG. 4(*d*) shows steps (F) and (G), and FIG. 4(*e*) shows step (H).

REFERENCE NUMERALS

Figure 1:
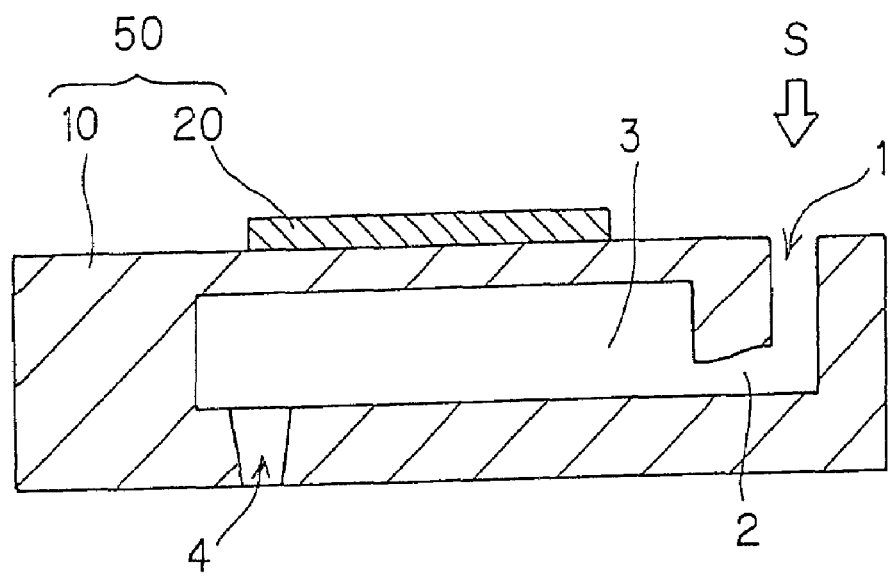
FIG. 1 is a schematic sectional view showing an embodiment of a method of producing a microarray according to the first aspect of the present invention.
Figure 1:
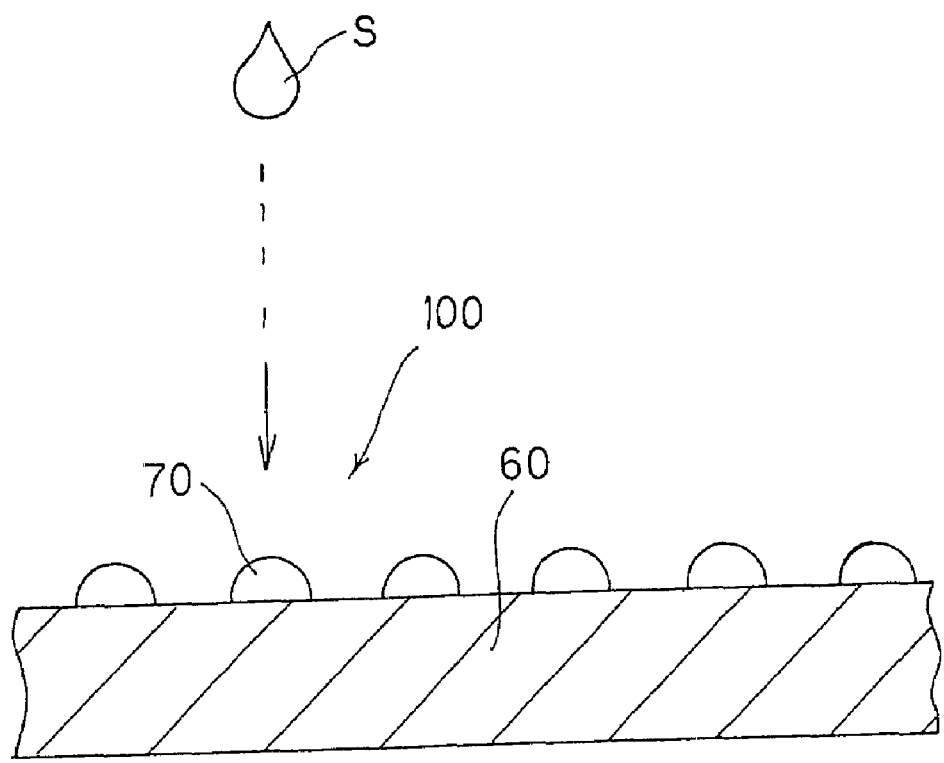

| | |
|---|---|
| 1 | inlet |
| 2 | channel |
| 3 | reservoir |
| 4 | outlet |
| 10 | substrate |
| 20 | piezoelectric/electrostrictive element |
| 50 | discharge unit |
| 51 | defective discharge unit |
| 52 | successful discharge unit |
| 53 | second defective discharge unit |
| 54 | second successful discharge unit |
| 60 | carrier |
| 65 | inspection carrier |
| 70 | sample spot |
| 71 | defective spot |
| 72 | successful spot |
| 73 | second defective spot |
| 74 | second successful spot |
| 75 | inspection spot |
| 100 | microarray |
| 102 | successful microarray |
| 103 | finished microarray |
| 104 | second successful microarray |
| 105 | finished microarray |
| 200 | apparatus for producing microarray |
| 210 | discharge head |
| 220 | tray |
| 230 | first movable table |
| 240 | second movable table |
| 250 | height control sensor |
| S | liquid sample |

BEST MODE FOR CARRYING OUT THE INVENTION

Referring to the drawings, embodiments of a method of producing a microarray according to a first aspect of the present invention will be described below in detail.

FIG. 1 is a schematic sectional view showing an embodiment of a method of producing a microarray according to this embodiment (the first aspect) of the present invention. As shown in FIG. 1, according to the first aspect of the present invention, using a plurality of discharge units 50 each comprising a substrate 10 and a piezoelectric/electrostrictive element 20; the substrate 10 including an inlet 1, a channel 2, a reservoir 3, and an outlet 4 of a liquid sample S, the liquid sample S discharged from the outlet 4 to outside is ejected onto a carrier or support 60 to form sample spots 70 corresponding to each discharge unit 50 on the carrier 60, and these steps are repeated for a plurality of liquid samples S as required, thereby providing a microarray 100 where a plurality of spots 70 comprising a plurality of liquid samples are aligned on the carrier 60 in a predetermined pattern.

Figure 2:
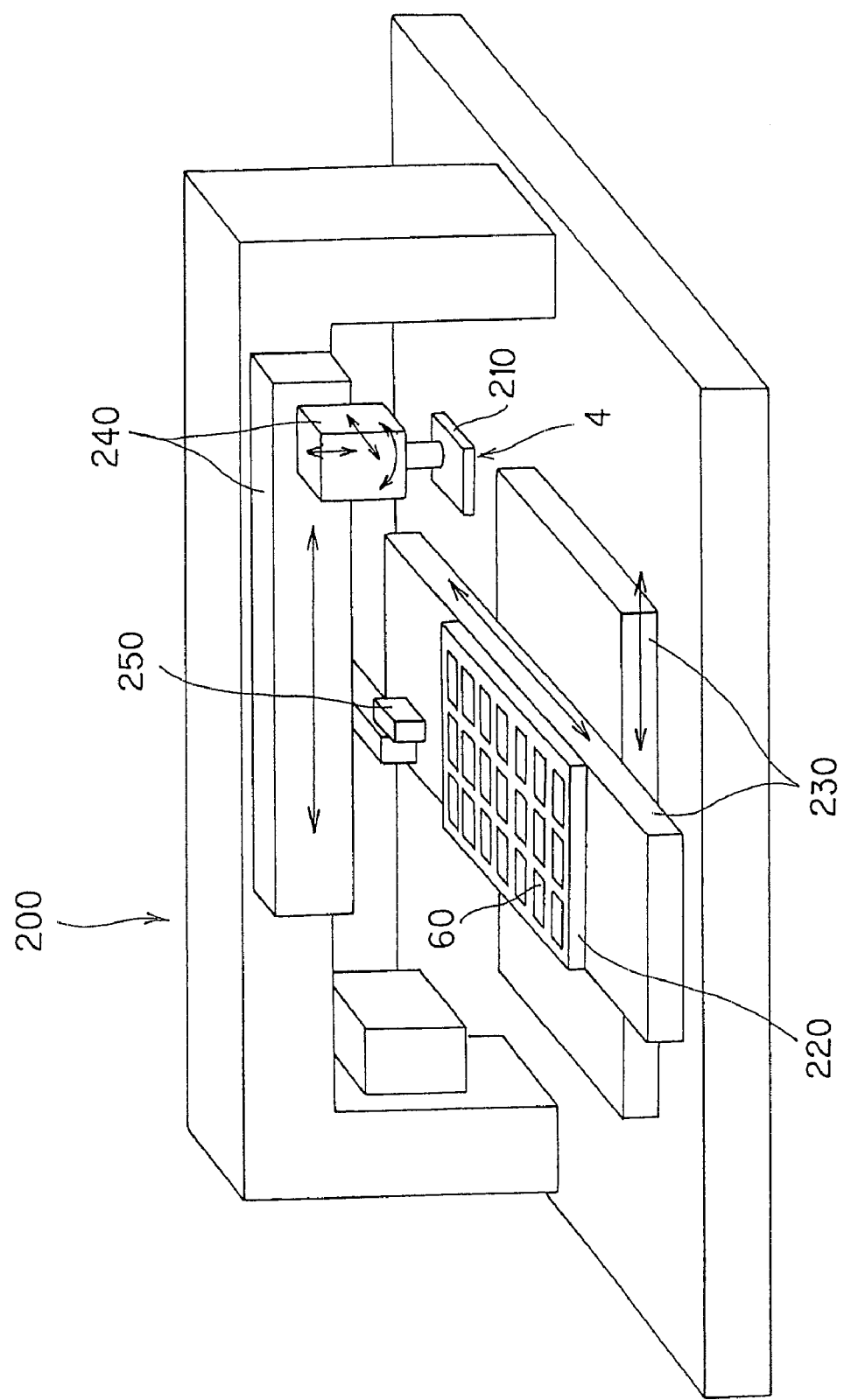
FIG. 2 is a schematic perspective view showing the apparatus for producing the microarray using in the embodiments according to the first and second aspect of the present invention.

Before the embodiment is described in detail, an apparatus for producing a microarray used in the embodiment will be described FIG. 2 is a schematic perspective view showing the apparatus for producing the microarray used in the embodiment. As shown in FIG. 2, an apparatus 200 for producing the microarray used in the embodiment comprises a discharge head 210, a tray 220, a first movable table 230, a second movable table 240, and a height control sensor 250 for the carrier. The discharge head 210 comprises one or more discharge modules (not shown) having one or more discharge units 50 (see FIG. 1). A slide glass is fixed on the tray 220 as one or more carriers 60 at a position opposing an outlet 4 of the discharge unit 50 (see FIG. 1) in the discharge head 210. The tray 220 is mounted movably on the first movable table 230. The first movable table 230 can be moved in X and Y directions and can move the position of the tray 220 (together with the carrier 60) so that the liquid sample S is discharged and ejected from the outlet 4 of the discharge unit 50 (see FIG. 1) in the discharge head 210 on a desired position of the carrier 60. The height control sensor 250 is disposed above the first movable table 230 to control the distance between the outlet 4 of the discharge head 210 and a spot surface of the carrier 60. A second movable table 240 on which the discharge head 210 is removably mounted can move the discharge head 210 in X, Y and Z directions and at an angle of rotation θ on an X-Y plane. The first movable table 230 on which the tray 220 is mounted and the second movable table 240 on which the discharge head 210 is removably mounted can be used to control the relative positions of the carrier 60 and the outlet 4.

Using this configuration, each liquid sample is introduced into the discharge head 210 in advance and is ejected to ensure that the drops of the liquid sample are properly discharged. Thereafter, the discharge head 210 is mounted on the second movable table 240, and the tray 220 on which a plurality of carriers 60 are fixed is mounted. Thus, spot formation can be conducted quickly and easily. This is effective especially when the properties of liquid sample, for example, a DNA-containing solution, an easily evaporated organic solvent, or a viscous easy-to-dry organic polymer-containing solution, changes rapidly with time by contact with the atmosphere once the discharge is started, and especially when the surface condition of the carrier 60, for example, a support coated with poly-L-lysine (PLL), changes rapidly due to the humidity in the air.

Also, it is especially effective when a DNA microarray is produced using a DNA-containing solution as the liquid sample, since tens to millions of spots should be disposed systematically without being ever overlapping within an area of only a few $mm^2$ to a few $cm^2$. For instance, when 1005 pieces of DNA microarrays each including carriers 60 each having 6048 spots are produced using the discharge head 210 having 96 pieces of outlets 4 on the tray 220, wherein 15 sheets of carriers 60 can be fixed, the discharge head 210 should be attached and detached to/from the second movable table 240 6048/96=63 times, and the tray 220 should be attached and detached to/from the first movable table 230 (1005/15)×63=4221 times. Accordingly, even if the mechanical accuracy in the mounted portions of the discharge head 210 and the tray 220 is improved, it is difficult to maintain it. This problem can be solved by using the control of positions of the movable tables and discharge heads as described above, thereby producing the DNA microarray on which the spots are arranged with high precision.

As shown in FIGS. 1 and 2, the spots 70 for a plurality of samples can be formed easily in a short time using the apparatus 200 for producing the microarray by, for example, injecting each liquid sample S from the inlet 1 of the corresponding discharge unit 50 to introduce them into the reservoir 3, discharging one of the liquid samples S introduced into the reservoir 3 as drops onto the carrier 60 at a predetermined position to form the sample spots 70 on the carrier 60, and repeating the steps for a plurality of liquid samples S.

Alternatively, a plurality of discharge heads 210 may be used. At least one of a plurality of liquid samples S is injected from the inlet 1 of each discharge unit 50 in each discharge head 210 and introduced into the reservoir 3. The discharge head 210 including the liquid sample S is mounted on the second movable table 240. The liquid sample S introduced into the reservoir 3 is discharged as drops at predetermined positions of the carrier 60, while the relative positions of the carrier 60 and the outlet 4 of the discharge head 210 are adjusted, whereby sample spots 70 comprising the liquid sample S are formed on the carrier 60. Then, the discharge head 210 is removed from the second movable table 240. Another discharge head including other liquid sample S (not shown) is mounted on the second movable table 240. The other liquid sample S introduced into the reservoir 3 is discharged as drops at the predetermined positions of the carrier 60, while the relative positions of the carrier 60 and the outlet 4 are adjusted, differently from the case of the former discharge head 210, whereby sample spots 70 comprising the other liquid sample S are formed on the carrier 60. The steps may be repeated according to the number of the discharge heads 210.

Alternatively, a plurality of trays 220 may be used. One of a plurality of trays 220 is mounted on the first movable table 230. The liquid sample S introduced into the reservoir 3 is discharged as drops at the predetermined positions of the carrier 60, while the relative positions of the carrier 60 fixed to the tray 220 and the outlet 4 are adjusted, whereby sample spots 70 comprising the liquid sample S contained in the discharge head 210 are formed on the carrier 60. Then, the tray 220 is removed from the first movable table 230. Another tray (not shown) to which another carrier (not shown) is fixed is mounted on the first movable table 230. The liquid sample S introduced into the reservoir 3 is discharged as drops at the predetermined positions of the other carrier (not shown), while the relative positions of the other carrier (not shown) and the outlet 4 are adjusted, whereby sample spots 70 comprising the liquid sample S contained in the discharge head 210 are formed on the other carrier. The steps may be repeated according to the number of the trays 220.

A combination of using a plurality of discharge heads 210 described above and using a plurality of trays 220 described above, i.e., a combination of a plurality of the discharge heads 210 including a plurality of the discharge units 50 and a plurality of the trays 220 to which a plurality of the carriers 60 are fixed, can be used to increase the number of types of liquid samples S and the number of the carriers 60, which can support the mass production of a variety of products.

Specifically, the liquid sample S containing the intended DNA and the like is discharged onto the carrier 60 held on the tray 220. The tray 220 with carrier 60 is removed from the first movable table 230. A new tray 220 including no sample spots 70 is mounted on the first movable table 230, and the liquid sample S is discharged thereto. This operation is repeated according to the intended number of the trays 220 with the carriers 60. The discharge head 210 is removed from the second movable table 240. Another discharge head (not shown) including the liquid sample S of another type of DNA and the like is mounted thereon. The sample spots 70 are formed on the carrier 60 on the tray 220. This configuration can provide the DNA microarray 100 on which many sample spots containing different kinds of DNA, for example ten thousand types of DNA, are formed.

Figure 3A:
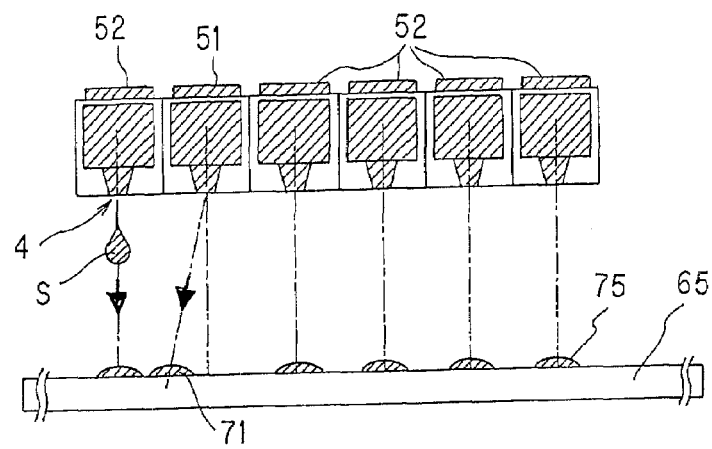
FIGS. 3(*a*) to 3(*c*) are schematic sectional views showing the embodiment of the method of producing the microarray according to the first aspect of the present invention.
Figure 3B:
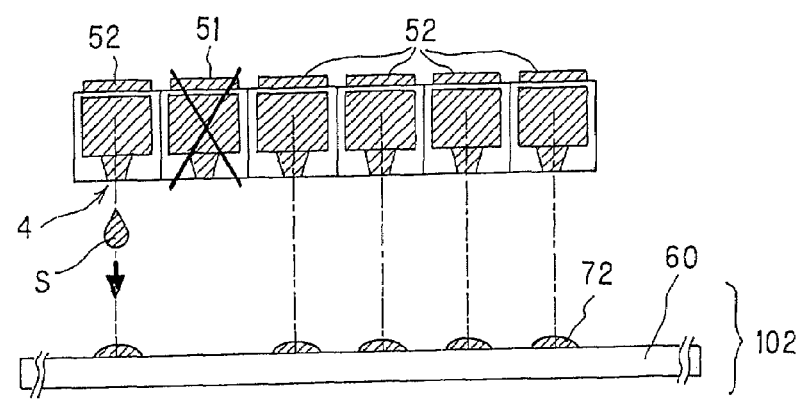
Figure 3C:
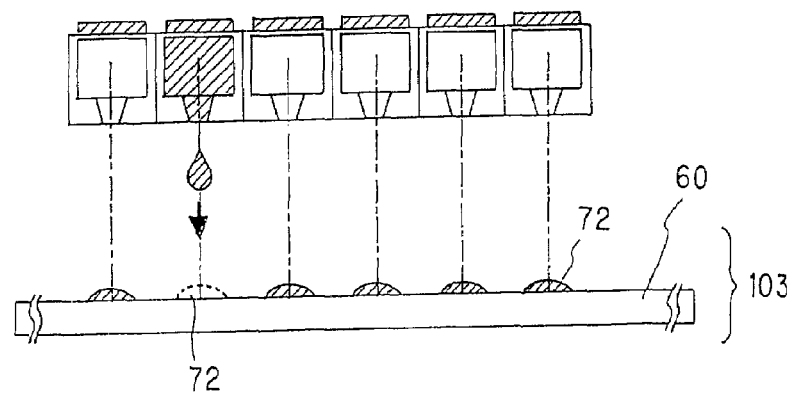
Figure 4A:
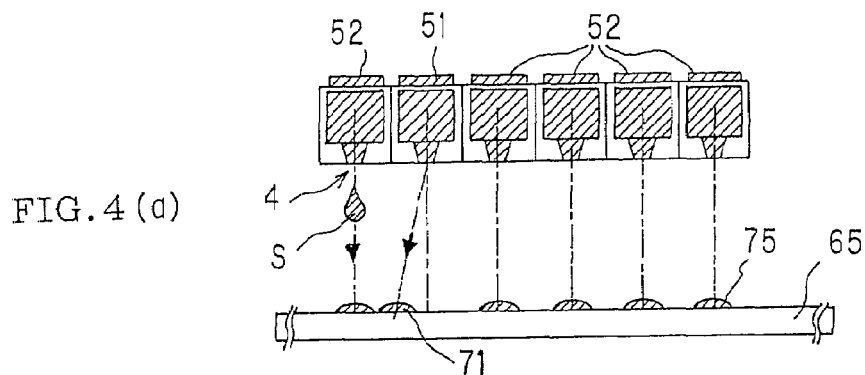
FIGS. 4(*a*) to 4(*e*) are schematic sectional views showing the embodiment of the method of producing the microarray according to the second aspect of the present invention.
Figure 4B:
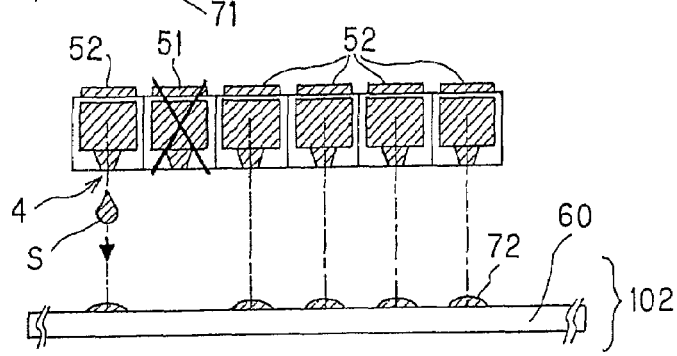
Figure 4C:
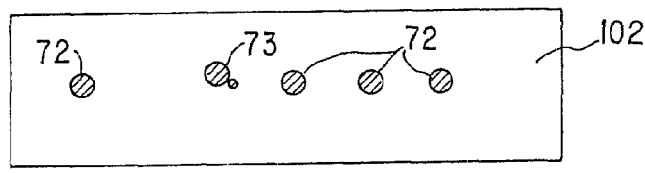
Figure 4D:
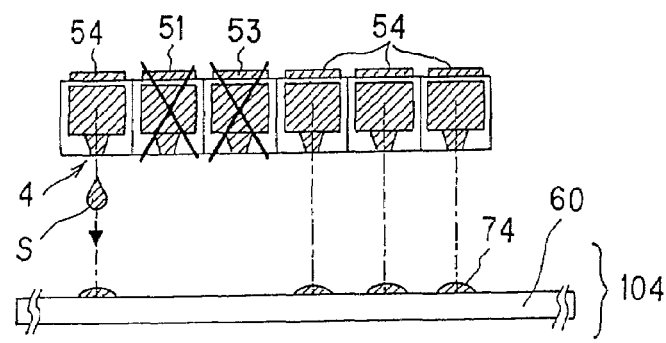
Figure 4E:
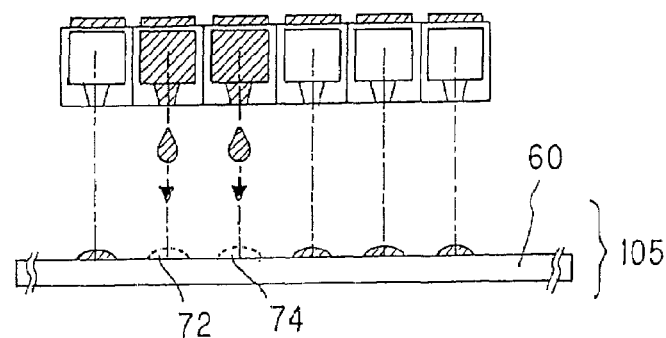

FIGS. 3(a) to 3(c) are schematic sectional views showing the embodiment of the method of producing the microarray according to the first aspect of the present invention. FIG. 3(a) shows step (A), FIG. 3(b) shows steps (B) and (C), and FIG. 3(c) shows step (D). The embodiment is achieved by steps (A), (B), (C) and (D) in combination with the disclosures shown in FIGS. 1 and 2. As shown in FIG. 3(a), in step (A), the liquid sample S discharged from the outlet 4 to outside is experimentally ejected onto an inspection carrier 65 to form inspection spots 75. The resultant inspection spots 75 are inspected for their quality to determine whether the inspected spots are defective or successful. Thus, the defective discharge unit 51, if any, can be detected. Then, as shown in FIG. 3(b), in step (B), the detected defective discharge unit 51 stops discharging the liquid sample S from the outlet 4 to outside, whereby the formation of the defective sample spot 71 from the defective discharge unit 51 is stopped. In step (C), successful sample spots 72 are formed on the carrier 60 using successful discharge units 52 excluding the defective discharge units 51, to provide a successful microarray 102 on which the successful spots 72 are aligned in a predetermined pattern on the carrier 60. As shown in FIG. 3(c), in step (D), a successful spot 72 to be formed originally is formed on the successful microarray 102 at the position of the defective spot 71 where no spot is formed in step (B), thereby providing a finished microarray 103 including the successful spots 72 aligned on the carrier 60 in a predetermined pattern. The phrase "when the inspection spot 75 is determined to be defective" herein corresponds to situations where the inspection spot is formed at the misaligned position since the discharge direction of the liquid sample is deviated with respect to the carrier 65, as shown in FIG. 3(a); where no spot is formed for some reason; where the diameter of the spot is too large or small; where there are undesired small spots known as satellites; or the like.

According to this embodiment, the inspection spots exclusively for inspection are formed on the inspection carrier, and are inspected for their quality. Thus, the formation of a defective spot on the product can be prevented. Also, the carrier exclusively for inspection is prepared, and it can be conveniently determined whether the inspected spots are defective or successful, thereby reducing the production time. In addition, according to this embodiment, the discharge only from the defective discharge unit(s) can be stopped and the successful discharge unit(s) can be used continuously without stopping the whole apparatus, including both the defective and successful discharge units, once a defective spot is produced. If all discharge units are stopped, it causes disadvantages such as precipitation, separation, or concentration change of the liquid sample within the discharge unit. According to this embodiment, these disadvantages are avoided since only the defective discharge units are stopped. The number of the defective spots, such as ring-shaped spots produced when a large number of microarrays are produced, can be decreased. The spots can be formed with high precision and high density, and can have stable shapes. Therefore, a microarray that is used for high-definition, high-speed analysis can be provided. The defective discharge units can be easily found during production, and the production history of the defective discharge units can be obtained. Thus, the working efficiency can be improved. The successful spots are produced in place of the defective spots in a separate or later step. As a result, a high-quality microarray including 100% successful spots can be provided.

In this embodiment, it is preferable that after the series of steps (A), (B) and (C) is repeated a plurality of times, step (D) be then conducted. When tens or more types of liquid samples are formed as spots on a carrier or support, steps (A), (B) and (C) are desirably conducted not only one time, but a plurality of times corresponding to a plurality of heads. Even though the tens or more types of liquid samples have different properties, they can be discharged from respective discharge heads under the optimum conditions. Therefore, a high-quality microarray having stable spot diameter and less misalignment can be provided. Typically, the liquid sample stopped in step (B) has significantly different properties from the liquid sample used in step (C) for providing the successful spots. Therefore, as step (D) is independent, the spot-forming conditions can be easily set to suit the properties of the liquid sample that may cause the defective spots. A plurality of liquid samples can be accommodated. When a series of the steps is repeated a plurality of times, the occurrence of the problems increases in proportion to the number of repetitions, and it is difficult to promptly find and avoid the failures. According to this embodiment, steps (A) and (B) are conducted repeatedly according to the number of liquid samples, whereby the failure can be found for each discharge head to avoid the failures immediately. Thus, the embodiment is especially effective when the microarray is produced by repeating the process steps.

The phrase "the series of steps (A), (B) and (C) is repeated a plurality of times" used herein means that the series of steps (A), (B) and (C) is repeated a plurality of times corresponding to a plurality of discharge heads for per each discharge head in a plurality of discharge heads to align successful spots 72 in a predetermined pattern on one or more carriers 60. Also, it can be applied to the situation in which when one head is used in the manufacturing process, steps (A), (B) and (C) are repeated a plurality of times for per each carrier or some carriers to align successful spots 72 in a predetermined pattern on a plurality of carriers 60 disposed on one or more trays (not shown), thereby providing a plurality of successful microarrays 102, or in which steps (A), (B) and (C) are repeated a plurality of times for per tray or some trays to align successful spots 72 in a predetermined pattern on a plurality of carriers 60 disposed on a plurality of trays (not shown), thereby providing a plurality of successful microarrays 102. In this way, the failures can be detected for each carrier (the minimum sample spot), for each tray, or for each specific number of carriers, thereby enhancing the yield of the arrays.

According to this embodiment, the formation of the defective spot 71 is stopped in step (B) preferably by completely drawing out the liquid sample S injected into the defective discharge unit 51. With this configuration, the liquid sample is not leaked from the apparatus, thus preventing the carrier from becoming contaminated. Even if the wrong signal is transmitted as the electrical signal for driving the piezoelectric/electrostrictive element 20, this ensures that the discharge of the liquid sample from the defective discharge unit 51 can be stopped and the formation of the defective spot 71 can be prevented.

In this case, it is preferable that the defective discharge unit 51 be further cleaned after the liquid sample is completely drawn out. In this way, the liquid sample S remaining in the channel 2, the reservoir 3, the outlet 4 and the like of the discharge unit 50 can be prevented from sticking and remaining thereto. The contamination caused by mixing it with a newly injected different liquid sample S can be thus prevented.

According to this embodiment, the formation of the defective spot 71 is stopped in step (B) preferably by stopping the transmittance of the electrical signal for driving the piezoelectric/electrostrictive element 20. When the liquid sample S is not easily dried and therefore can be easily cleaned after standing, the discharge of the liquid sample from the defective discharge unit 51 can be stopped conveniently in a short time to prevent the formation of the defective spot 71.

According to this embodiment, it is preferable that the distance between the inspection carrier 65 and the outlet 4 be set to be greater when the inspection spots 75 are formed in step (A) than the distance between the carrier 60 and the outlet 4 when the successful spots 72 are formed in step (C). In this way, the accuracy of the inspection for detecting the misaligned position of the spots caused by deviating the discharge direction from the desired direction can be enhanced.

According to this embodiment, when a plurality of successful microarrays 102 are formed, the successful spot 72 to be formed originally is formed in step (D) in a reverse order in step (C) on the successful microarray 102 at the position of the defective spot 71 where no spot is formed in step (B). The phrase "formed in a reverse order" means that the sequence of forming spots on the trays on which one or more carriers are held is reversed, or means that the sequence of trays on which one or more carriers are held is reversed. When using one head, steps (A), (B) and (C) are conducted a plurality of times on a plurality of carriers 60 per carrier 60 which are fixed on one or more trays (not shown), or steps (A), (B) and (C) are conducted on a plurality of carriers 60 a plurality of times for each tray (not shown), the number of blanks where no spot is formed in step (B) is increased in proportion to the number of times of steps (A), (B) and (C). Accordingly, reversing the order in step (D) allows starting to form a successful spot at the position of the defective spot where no spot is formed in step (B) on the carrier having more blanks. Thus, the arrays can be effectively produced. Specifically, the successful spots are first formed using a plurality of discharge units for the carrier(s) having many blanks, then using fewer discharge units for the carrier(s) having less blanks. The number of the discharge units can be gradually decreased, whereby step (D) can be completed in a short time. According to this embodiment, the production history of the defective discharge unit 51 can be obtained, as described above. Utilizing the production history, the sample spots, i.e., the successful spots 52 to be formed originally can be effectively formed in a short time.

A method of producing a microarray in an embodiment according to the second aspect of the present invention will be described. According to the second aspect, similar to the first embodiment, as shown in FIG. 1, a plurality of discharge units 50 each including a substrate 10 and a piezoelectric/electrostrictive element 20; the substrate 10 having an inlet 1, a channel 2, a reservoir 3, and an outlet 4 of a liquid sample S, the liquid sample S discharged from the outlet 4 to outside is ejected onto a carrier or support 60 to form a sample spot 70 corresponding to each discharge unit 50 on the carrier 60, and these steps are repeated for a plurality of liquid samples S as required, thereby providing a microarray 100 where a plurality of spots 70 comprising a plurality of liquid samples are aligned on the carrier 60 in a predetermined pattern. The apparatus for producing the microarray used in the second aspect is the same as described in the first aspect as shown in FIG. 2.

FIGS. 4(*a*) to 4(*e*) are schematic sectional, views showing the embodiment of the method of producing the microarray according to the second aspect of the present invention. FIG. 4(*a*) shows step (A), FIG. 4(*b*) shows steps (B) and (C), FIG. 4(*c*) shows step (E), FIG. 4(*d*) shows steps (F) and (G), and FIG. 4(*e*) shows step (H). The embodiment is achieved by steps (A), (B), (C), (E), (G), (F) and (H) in combination with the disclosures shown in FIGS. 1 and 2. Steps (A), (B) and (C) are described above in the first aspect. As shown in FIG. 4(*a*), in step (A), the liquid sample S discharged from the outlet 4 to outside is experimentally ejected onto an inspection carrier 65 to form inspection spots 75. The resultant inspection spots 75 are inspected for their quality to determine whether the inspected spots are defective or successful. Thus, the defective discharge unit 51, if any, can be detected. Then, as shown in FIG. 4(*b*), in step (B), the detected defective discharge unit 51 stops discharging the liquid sample S from the outlet 4 to outside, whereby the formation of the defective sample spots from the defective discharge unit 51 is stopped. In step (C), successful sample spots 72 are formed on the carrier 60 using successful discharge units 52 excluding the defective discharge units 51, to provide a successful microarray 102 on which the successful spots 72 are aligned in a predetermined pattern on the carrier 60. As shown in FIG. 4(*c*), in step (E), the quality of the resultant successful spots 72 of the successful microarray 102 is inspected to detect a second defective discharge unit 53 (see FIG. 4(*d*)). As also shown in FIG. 4(*d*), in step (F), the detected second defective discharge unit 53 stops discharging the liquid sample S from the outlet 4 to outside, whereby the formation of a second defective sample spot 73 (see FIG. 4(*c*)) from the second defective discharge unit 53 is stopped. In step (G), second successful sample spots 74 are formed on the carrier 60 using second successful discharge units 54 excluding the defective discharge units 51 and the second defective discharge units to provide a second successful microarray 104 on which the second successful spots 74 are aligned in a predetermined pattern on the carrier 60. As shown in FIG. 4(*e*), in step (H), a successful spot 72 and a second successful spot 74, both to be formed originally, are formed on the second successful microarray 104 (see FIG. 4(*d*)) at the position of the defective spot 71 (see FIG. 4(*a*)) and the second defective spot 73 (see FIG. 4(*c*)) where no spots are formed in steps (B) and (E), thereby providing a finished microarray 105 including the successful spots 72 and the second successful spots 74 aligned on the carrier 60 in a predetermined pattern.

According to this embodiment, when a very large number of the microarrays are produced, the detection of the defective discharge unit during production meets the actual conditions and can be done more precisely. The quality of the resultant microarray and the working efficiency can be further improved. In step (E), the quality of the successful spots 72 of the resultant successful microarray 102 may be inspected per carrier. In the case of producing the microarray by the inkjet method, most of the successful spots remain successful while a plurality of spots are formed or a plurality of carriers are treated. From the viewpoint of the working efficiency, the quality of the successful spots 72 is inspected per some carriers, the tray on which the carriers are fixed, or some trays, depending on the types of the sample solution spotted and the properties of the discharge unit. If the spots are formed with stability such that the inspected result of the spots 72 is almost all successful, at the same time of step (E), the second successful spots may be formed on the carrier in respect to the second successful discharge unit other than the defective and the second defective discharge units (not yet in existence) in step (G). The whole steps can proceed very rapidly. In the event that the defective spot is detected in step (E) conducted simultaneously in step (G), only the microarray including the defective spot which is formed in step (G) is detected as defective. It can prevent that the successful and defective microarrays from considering defective as a whole. Thus, both the yields and the shortening of the process time can be attained in a reasonable level.

In the embodiment, it is preferable that after the series of steps (A), (B), (C), (E), (F) and (G) be repeated a plurality of times, step (H) be then conducted. The intent and the significance are the same as in the first embodiment.

The phrase "the series of steps (A), (B), (C), (E), (F) and (G) is repeated a plurality of times" used herein means that the series of steps (A), (B), (C), (E), (F) and (G) is repeated a plurality of times corresponding to a plurality of discharge heads for each discharge head in a plurality of discharge heads to align successful spots 72 and 74 in a predetermined pattern on one or more carriers 60. Also, it can be applied to the situation in which when one head is used in the manufacturing process, steps (A), (B) and (C) are conducted on a plurality of carriers 60 disposed on one or more trays (not shown), then steps (E), (F) and (G) are repeated a plurality of times for per each carrier or some carriers, or per tray or some trays (not shown) to align successful spots 74 in a predetermined pattern, thereby providing a plurality of second successful microarrays 104. In this way, by repeating steps (E), (F) and (G) a plurality of times per some trays, the failures can be detected efficiently per the specific numbers of the carriers, thereby shortening the production time and enhancing the yields of the arrays simultaneously.

When a plurality of heads are used, steps (A), (B), (C), (E), (F) and (G) are conducted using the first head, and then steps (C), (E), (F) and (G) are repeated using the second or later heads.

The above-described combinations of the steps can be suitably used in the case that there is less variety between the properties of the liquid samples, i.e., oligo-DNA-containing liquid samples, to be discharged using a plurality of heads, and the first head is used in steps (A) and (B) and the other heads are then used, thereby shortening the production time. In this case, when the first head is used in the manufacturing process, steps (E), (F) and (G) are repeated a plurality of times per some trays when the spot-forming is made on a plurality of carriers on a plurality of trays.

Figure 5:
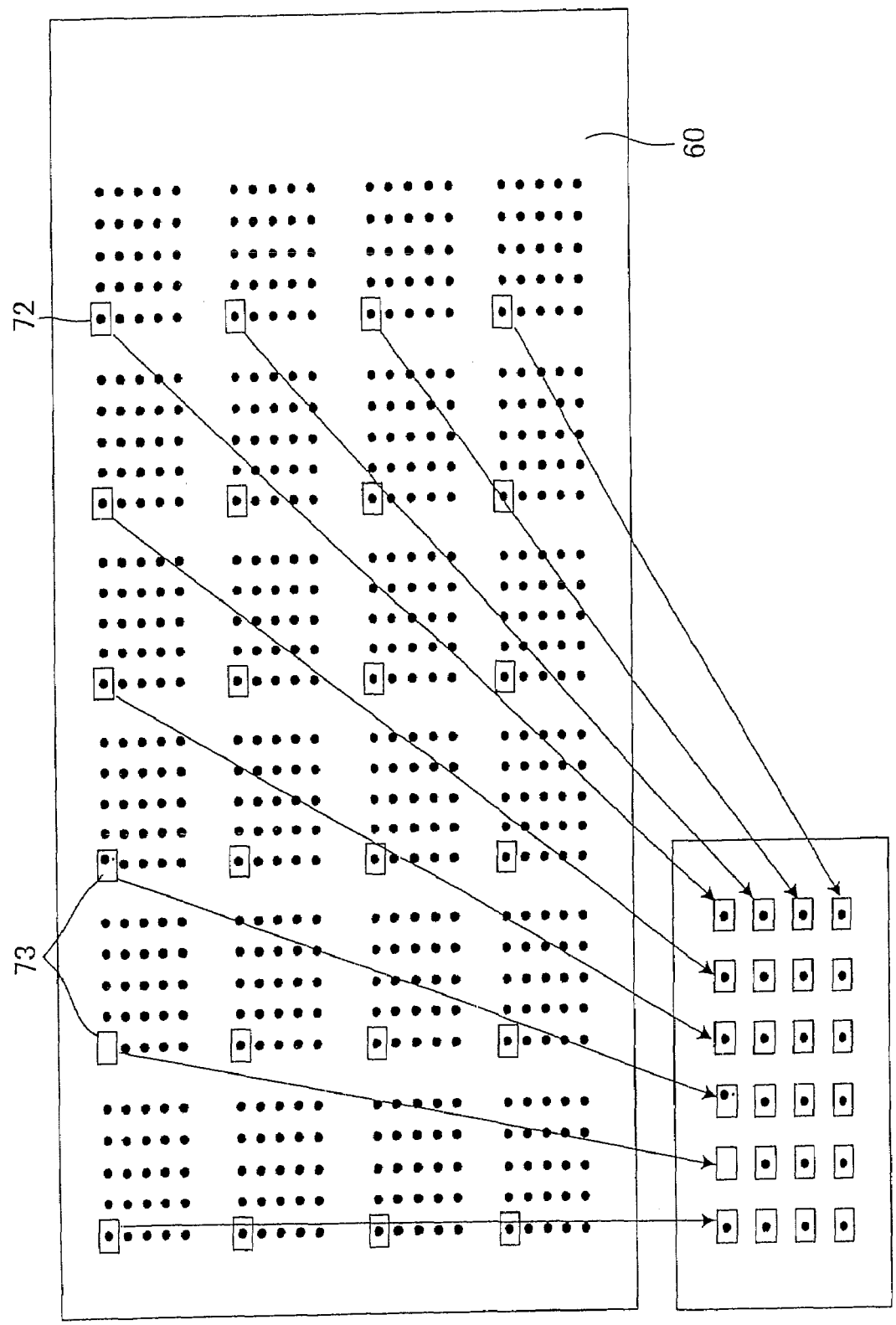
FIG. 5 is a schematic plan view showing that in step (E) the embodiment of the method of producing the microarray according to the first aspect of the present invention, the quality of the successful spots on the resultant successful microarray is preferably inspected with the human eye using a display means capable of displaying in a noticeable manner only the successful spots formed simultaneously, and is determined whether they are defective or successful, thereby detecting the defective discharge unit.

According to this embodiment, as shown in FIG. 5, in step (E), the quality of the successful spots 72 on the resultant successful microarray 102 (see FIG. 4(*b*)) is preferably inspected using a display means capable of displaying in a noticeable manner only the successful spots 72 formed simultaneously, and also with the human eye to determine whether they are defective or successful to detect the defective spot 73, whereby detecting the second defective discharge unit 53, as shown in FIG. 4(*d*). Typically, when the microarray contains the spots aligned with a very high density, it is often difficult to provide the adjacent spots simultaneously by adjacent discharge units, since decreasing the distance between discharge units is limited. Therefore, the spots formed simultaneously are often disposed discretely over the array, as shown in FIG. 5. When a certain spot is selectively inspected, it should be observed widely. It requires time and effort to identify and inspect the spot in detail. Therefore, the above-described method can simplify the inspection and evaluate adequately. The way that only the intended spots are inspected using the display means capable of displaying in a noticeable manner only the intended spots and with the human eyes can not only be applied to step (E), but also to step (A) where the liquid sample is experimentally ejected onto an inspection carrier 65 (see FIG. 4(*a*)) to form inspection spots 75 (see FIG. 4(*a*)), and the resultant inspection spots are inspected.

According to this embodiment, the formation of the defective spot 71 and/or the second defective spot 73 corresponding to the defective discharge unit 51 and/or the second defective discharge unit 53 is stopped in step (B) and/or (F) preferably by completely drawing out the liquid sample S injected into the defective discharge unit 51 and/or the second defective discharge unit 53. The intent and the significance are the same as in the first embodiment.

In this case, it is preferable that the defective discharge unit 51 and/or the second defective discharge unit 53 be further cleaned after the liquid sample is drawn out. The intent and the significance are the same as in the first embodiment.

According to this embodiment, the formation of the defective spot 71 and/or the second defective spot 73 corresponding to the defective discharge unit 51 and/or the second defective discharge unit 53 is stopped in step (B) and/or (F) preferably by stopping the transmittance of the electrical signal for driving the piezoelectric/electrostrictive element 20. The intent and the significance are the same as in the first embodiment.

According to this embodiment, it is preferable that the distance between the inspection carrier 65 and the outlet 4 when the inspection spots 75 are formed in step (A) be set to be greater than the distance between the carrier 60 and the outlet 4 when the second successful spots 74 are formed in step (G). The intent and the significance are the same as in the first embodiment.

According to this embodiment, the successful spot and the second successful spot 72, 74 to be formed originally are preferably formed in a reverse order on the second successful microarray 104 at the position of the defective spot and the second defective spot 71, 73 where no spots are formed in step (H). The intent and the significance are the same as in the first embodiment.

In the first and second aspects of the present invention, biological samples including RNA, protein, antibody, cell and the like as well as DNA can be used as the liquid sample S. The first and second aspects of the present invention are especially effective to use the liquid that requires the spots that are formed stably with high precision and high density and for high-definition, high-speed analysis.

Non-limiting materials can be used for the substrate 10 of the discharge unit 50 used in the first and second aspects of the present invention. For example, the portion on which the reservoir 3 is at least formed and the portion on which piezoelectric/electrostrictive element 20 are disposed are preferably composed of zirconia ceramics. More preferably, all portions of the substrate 10 are composed of zirconia ceramics. Zirconia, among others, stabilized zirconia and partially stabilized zirconia are preferable materials of the substrate 10 according to the present invention, since they have high mechanical strength even if they are sheet, have high toughness, are durable to both acid and alkali solutions, and are less reactive to a piezoelectric film and an electrode material. In this case, it is preferable that the zirconia ceramics be produced by a green sheet laminate sintering method. In other words, the substrate 10 is preferably produced by laminating a ceramic sheet (i.e., green sheet) and sintering the laminate, since a complex hollow structure can be easily formed as a sintered body. In addition, the portion of the substrate 10 on which the outlet 4 is formed may be composed of resin from moldability and cost viewpoints.

The piezoelectric/electrostrictive element 20 for use in the first and second aspects of the present invention is not especially limited, but is preferably composed of a piezoelectric/electrostrictive film containing at least one lead compound selected from the group consisting of lead zirconate, lead titanate and magnesium lead niobate. The piezoelectric/electrostrictive film is preferable in that it has a high electromechanical coupling factor and a high piezoelectric constant, is less reactive to the substrate 10 composed of zirconia ceramics when the piezoelectric film is sintered, and provides the stable composition.

The microarray according to the third aspect of the present invention is produced by any methods as described above, and has spots that are formed stably with high precision and high density and are used for high-definition, high-speed analysis.

The following non-limiting examples further illustrate the present invention.

EXAMPLE 1

The microarray of EXAMPLE 1 was produced using the following procedures (1) to (5) under the following condition (A).

[Condition (A)]
Number of discharge holes per head: 96
Kinds of liquid samples: 96
Liquid sample: c-DNA solution dissolved in 10 mM of phosphate buffer (containing 0.1 µg/µL of c-DNA)
Carrier: Poly-L-lysine (PLL) coated slide glass, having a size of 76 mm×26 mm×1 mm (thick)
Spot pattern: 12 rows×8 columns, 0.3 mm pitch, spot diameter 120 µm
Number of microarrays produced: 400
Number of trays: 20 (20 trays each having 20 carriers were used)

[Procedures (1) to (5)]
(1) Before the liquid sample was practically spotted on a carrier on the first tray and a carrier on the next tray, step (A) was conducted. Specifically, the liquid sample discharged from the outlet to outside was experimentally ejected onto an inspection carrier to form inspection spots. The resultant inspection spots were inspected for their quality to determine whether the inspected spots were defective or successful. Thus, the defective discharge unit(s), if any, was(were) detected. The quality of the spots experimentally spotted on the inspection carrier was inspected as follows: Were there no spots formed? Did the spots have irregular shapes? Did the spot diameter deviate 10% or more? Were there unnecessary spots known as satellites? In addition, before the liquid sample was practically spotted on the carrier on the first tray, after step (A), using the distance between the carrier and the outlet was 4 mm that was 10 times of that, i.e., 0.4 mm, used in the normal step (step (C), successful sample spots were formed on the carrier using successful discharge units, to provide a successful microarray on which the successful spots were aligned in a predetermined pattern on the carrier), the liquid sample was experimentally ejected, and the inspection was conducted whether or not the position of the ejected spot was deviated 0.2 mm or more from the initial designed position.
(2) The discharge units detected as defective in the procedure (1) was subjected to step (B). Specifically, the detected defective discharge unit was stopped to discharge the liquid sample from the outlet to outside, whereby the formation of the defective sample spots from the defective discharge unit was stopped. The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).
(3) Step (C) was conducted. Specifically, successful sample spots were formed on 20 pieces of the carrier held on the tray using successful discharge units, to provide a successful microarray on which the successful spots were aligned in a predetermined pattern on the carriers.
(4) Steps (A), (B) and (C) were conducted to 20 pieces of the trays in the order of Nos. 1, 2, 3 . . . 20.

(5) After the successful spots were formed on 20 pieces of the trays including 400 pieces of carriers, step (D) was conducted. Specifically, a successful spot to be formed originally was formed on the successful microarray at the position of the defective spot where no spot is formed in step (B), thereby providing a finished microarray including the successful spots aligned on the carriers in a predetermined pattern. The successful spots were formed on the trays in the reverse order of Nos. 20, 19, 18 . . . 1.

EXAMPLE 2

The procedures of EXAMPLE 1 were essentially repeated except that in the procedure (2) the formation of the defective spots was stopped by stopping the transmittance of the electrical signal for driving the piezoelectric/electrostrictive element of the defective discharge unit that provided the defective spots instead of the following: The formation of the defective sample spots was stopped conveniently by inserting a pipette or the like from the inlet of the discharge unit of interest, and aspirating the liquid to completely draw out the liquid sample. Then, 200 μl of pure water was injected from the inlet, the outlet was vacuum-aspirated, and the injection and the aspiration were repeated to clean the defective discharge unit(s)

Comparative Example 1

The microarray of COMPARATIVE EXAMPLE 1 was produced using the following procedures (1) to (9) under the above-described condition (A).

[Procedures (1) to (9)]
(1) A magnification camera was used to determine the presence or absence of the spots discharged from the discharge head, and the failure or no failure in the discharged direction (no failure was within ±3 degree in the vertical direction). After the determination, the defective discharge unit was tried to improve by adjusting the driving signal transmitted to the piezoelectric/electrostrictive element. Specifically, the driving signal was adjusted by changing the voltage value, the rise time to the predetermined voltage value, the time for keeping the predetermined voltage value, the voltage falling time and the like.
(2) When the aforementioned procedure (1) was not succeeded, the liquid sample was drawn out from the discharge unit of interest, i.e., by inserting a pipette or the like into the inlet to aspirate the liquid sample. Then, the liquid sample was again injected to inspect the discharged drops.
(3) The procedures (1) and (2) were repeated until all discharged drops were discharged from all discharge holes with certainty.
(4) Using all successful discharge units, successful sample spots were formed on 20 pieces of the carrier held on the tray No. 1 to provide a successful microarray on which the successful spots were aligned in a predetermined pattern on the carriers.
(5) Before proceeding with the next tray, the carrier on the tray formed immediately before was drawn out to inspect the spots. If the spots were defective, the driving signal transmitted to the piezoelectric/electrostrictive element of the discharge unit of interest was readjusted.
(6) If it was not succeeded by readjusting the driving signal, the liquid sample was drawn out from the discharge unit of interest by inserting the pipette or the like from the inlet of the discharge unit, and injecting again the liquid sample to inspect the spots.
(7) The procedures (5) and (6) were repeated until all discharged drops were discharged from all discharge holes with certainty.
(8) Using all successful discharge units, successful sample spots were formed on 20 pieces of the carrier held on the tray No. 2 to provide a successful microarray on which the successful spots were aligned in predetermined pattern on the carriers.
(9) The procedures (5), (6), (7) and (8) were conducted to 20 pieces of the trays in the order of Nos. 1, 2, 3 . . . 20.

(Evaluation) After all spots were formed, the microarrays of EXAMPLES 1 and 2 and COMPARATIVE EXAMPLE 1 were humidified by cooling to −20° C., and allowing them to stand at 22.5° C. and at humidity of 26%, baked at 80° C. for 1 hour, blocked by cleaning them with sterile purified water 3 times, immersing them into boiled water for 3 minutes and then into ethanol for 1 minute and hybridizing with fluorescent c-DNA to evaluate the spots. Specifically, the quality of the spots was determined by the number of ring failures having significantly different fluorescent values between the perimeter and the center. In this evaluation, the ring failure was defined as 10/1 or more fluorescent ratio of the perimeter to the center. A position accuracy of the spots was evaluated by measuring the displacement from the design positions using a microscope. When the spot was displaced ⅓ (40 μm) or more from the designed spot diameter, such a spot was defective.

(Results) The evaluation results are shown in Table 1.

TABLE 1

| | Number of spots formation stopped in procedures (1) to (5) | Process time (hrs) | Number of defective rings (average number of 400 carriers) | Number of displaced spots (average number of 400 carriers) |
|---|---|---|---|---|
| EX. 1 | 2 | 2 | 0.8 | 0 |
| Ex. 2 | 2 | 1.5 | 0.5 | 0 |
| COMP. EX. 1 | (Note 1) | 5 | 20 | 5 |

(Note 1):
The signal adjustment and the unit exchange were repeated until the stop of forming the spots were ended.

In EXAMPLE 2, it required 3 times greater amount of the cleaner, and 5 times longer time than normal for cleaning after the formation of the spots was stopped.

The results show that EXAMPLES 1 and 2 are effective for the decrease in the ring failures and the increase in the position accuracy.

EXAMPLE 3

The microarray of EXAMPLE 3 was produced using the following procedures (1) to (13) under the following condition (B)

[Condition (B)]
Number of discharge holes per head: 96
Kinds of liquid samples: 960
Liquid sample: c-DNA solution dissolved in 25 mM of TE buffer (containing 0.2 μg/μL of c-DNA)
Carrier: Poly-L-lysine (PLL) coated slide glass, having a size of 76 mm×26 mm×1 mm (thick)
Spot pattern: 12 rows×8 columns, 0.3 mm pitch, spot diameter 120 μm Number of microarrays produced: 800
Number of trays: 40 (one tray each having 20 carriers were used)

[Procedures (1) to (13)]
(1) The first head containing first 96 types of c-DNAs among 960 types was subjected to step (A). Specifically, the liquid sample discharged from the outlet to outside was experimentally ejected onto an inspection carrier to form inspection spots. The resultant inspection spots were inspected for their quality to determine whether the inspected spots were defective or successful. Thus, the defective discharge unit(s), if any, was(were) detected. The quality of the spots experimentally spotted on the inspection carrier was inspected as follows: Were there no spots formed? Did the spots have irregular shapes? Did the spot diameter deviate 10% or more? Were there unnecessary spots known as satellites? In addition, using the distance between the carrier and the outlet was 4 mm that was 10 times of that, i.e., 0.4 mm, used in the normal step (step (C), successful sample spots were formed on the carrier using successful discharge units, to provide a successful microarray on which the successful spots were aligned in a predetermined pattern on the carrier), the liquid sample was experimentally ejected, and the inspection was conducted whether or not the position of the ejected spot was deviated 0.2 mm or more from the initial designed position.

(2) The discharge units detected as defective in the procedure (1) were subjected to step (B). Specifically, the detected defective discharge unit was stopped to discharge the liquid sample from the outlet to outside, whereby the formation of the defective sample spots from the defective discharge unit was stopped. The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).

(3) 5 trays (20 pieces×5=100 pieces) were subjected to step (C). Specifically, successful sample spots were formed on 20 pieces of the carrier held on the tray using successful discharge units, to provide a successful microarray on which the successful spots were aligned in a predetermined pattern on the carriers.

(4) In the procedure (3), after the first successful spots without liquid aspiration in the procedure (2) were formed, the fifth tray on which the spots were formed finally was subjected to step (E). Specifically, the quality of the resultant successful spot of the successful microarray was inspected to detect a second defective discharge unit. The first successful spots were inspected for their quality using an inspection apparatus capable of displaying in a noticeable manner only the discharged spots by one head. Specifically, the quality of the spots was inspected mechanically with an image processing by a computer and CCD, a decision circuit, and also inspected visually by the operator as follows: Were there no spots formed? Did the spots have irregular shapes? Did the spot diameter deviate 10% or more? Were there unnecessary spots known as satellites?

(5) The defective discharge unit, if any, detected in the procedure (4) was subjected to step (F). Specifically, the detected second defective discharge unit was stopped to discharge the liquid sample from the outlet to outside, whereby the formation of a second defective sample spot from the second defective discharge unit is stopped. The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).

(6) The next 5 trays (20 pieces×5 trays=100 pieces) were subjected to step (G). Specifically, second successful sample spots were formed on the carrier using second successful discharge units to provide a second successful microarray on which the second successful spots were aligned in a predetermined pattern on the carrier.

(7) In step (G), after the second successful, spots without liquid aspiration in step (F) were formed, the fifth tray on which the spots were formed finally was subjected to step (E). Specifically, the quality of the resultant successful spot of the successful microarray was inspected to detect a second defective discharge unit. The second successful spots were inspected for their quality using an inspection apparatus capable of displaying in a noticeable manner only the discharged spots by one head. Specifically, the quality of the spots was inspected mechanically with an image processing by a computer and CCD, a decision circuit, and also inspected visually by the operator as follows: Were there no spots formed? Did the spots have irregular shapes? Did the spot diameter deviate 10% or more? Were there unnecessary spots known as satellites?

(8) The defective discharge unit, if any, detected in step (E) was subjected to step (F). Specifically, the detected second defective discharge unit was stopped to discharge the liquid sample from the outlet to outside, whereby the formation of a second defective sample spot from the second defective discharge unit is stopped. The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).

(9) The next 5 trays (20 pieces×5 trays=100 pieces) were subjected to step (G). Specifically, second successful sample spots were formed on the carrier using second successful discharge units to provide a second successful microarray on which the second successful spots were aligned in a predetermined pattern on the carrier.

(10) The procedures (7), (8) and (9) were repeated 5 times to produce successful spots on 800 pieces of the carriers held on 40 pieces of the trays.

(11) The head containing the next 96 types of c-DNAs was subjected to the aforementioned procedures (1) to (10). Using 192 types of c-DNAs in total, the successful spots were formed on 800 pieces of the carriers.

(12) The remaining 8 heads containing 960 types of c-DNAs were subjected to the aforementioned procedures (1) to (10). Using 960 types of c-DNAs in total., the successful spots were formed on 800 pieces of the carriers.

(13) After the successful spots were formed on 40 pieces of the trays including 800 pieces of carriers, step (H) was conducted. Specifically, a successful spot and a second successful spot, both to be formed originally, were formed on the second successful microarray at the position of the defective spot and the second defective spot where no spots were formed in steps (B) and (E), thereby providing a finished microarray including the successful spots and the second successful spots aligned on the carrier 60 in a predetermined pattern. In other words, the successful spots were formed in the positions where no spots were formed in the aforementioned procedures (3), (6), (9), (10), (11) and (12). The successful spots were formed on the trays in the reverse order of the procedures (12), (11), (10), (9), (6) and (3).

EXAMPLE 4

The procedures of EXAMPLE 3 were essentially repeated except that in the procedures (2), (5), (8), (10), (11) and (12) the formation of the defective spots was stopped by stopping the transmittance of the electrical signal for driving the piezoelectric/electrostrictive element of the defective discharge unit that provided the defective spots instead of the following: The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).

EXAMPLE 5

The microarray of EXAMPLE 5 was produced using the following procedures (1) to (6) under the following condition (B).

[Procedures (1) to (6)]
(1) The first head containing first 96 types of c-DNAs among 960 types was subjected to step (A). Specifically, the liquid sample discharged from the outlet to outside was experimentally ejected onto an inspection carrier to form inspection spots. The resultant inspection spots were inspected for their quality to determine whether the inspected spots were defective or successful. Thus, the defective discharge unit(s), if any, was(were) detected. Specifically, the quality of the spots experimentally spotted on the inspection carrier was inspected as follows: Were there no spots formed? Did the spots have irregular shapes? Did the spot diameter deviate 10% or more? Were there unnecessary spots known as satellites? In addition, using the distance between the carrier and the outlet was 4 mm that was 10 times of that, i.e., 0.4 mm, used in the normal step (step (C), successful sample spots were formed on the carrier using successful discharge units, to provide a successful microarray on which the successful spots were aligned in a predetermined pattern on the carrier), the liquid sample was experimentally ejected, and the inspection was conducted whether or not the position of the ejected spot was deviated 0.2 mm or more from the initial designed position. The inspection spots were inspected for their quality using an inspection apparatus capable of displaying in a noticeable manner only the discharged spots by one head. Specifically, the quality of the spots was inspected mechanically with an image processing by a computer and CCD, a decision circuit, and also inspected visually by the operator.
(2) The discharge units detected as defective in the procedure (1) were subjected to step (B). Specifically, the detected defective discharge unit was stopped to discharge the liquid sample from the outlet to outside, whereby the formation of the defective sample spots from the defective discharge unit was stopped. The formation of the defective sample spots was stopped conveniently by inserting a pipette or the like from the inlet of the discharge unit of interest, and aspirating the liquid to completely draw out the liquid sample. Then, 200 µl of pure water was injected from the inlet, the outlet was vacuum-aspirated, and the injection and the aspiration were repeated to clean the defective discharge unit(s).
(3) Step (C) was conducted. Specifically, successful sample spots were formed on 20 pieces of the carrier held on the tray using successful discharge units, to provide a successful microarray on which the successful spots were aligned in a predetermined pattern on the carriers.
(4) Steps (A), (B) and (C) were conducted to 40 pieces of the trays in the order of Nos. 1, 2, 3 . . . 40.
(5) The remaining 9 heads containing 960 types of c-DNAs were subjected to the aforementioned procedures (1) to (4). Using 960 types of c-DNAs in total, the successful spots were formed on 40 pieces of the trays including 800 pieces of the carriers. However, after step (A), the following inspection was not conducted: using the distance between the carrier and the outlet was 4 mm that was 10 times of that, i.e., 0.4 mm, used in the normal step (step (C), successful sample spots were formed on the carrier using successful discharge units, to provide a successful microarray on which the successful spots were aligned in a predetermined pattern on the carrier), the liquid sample was experimentally ejected, and the inspection was conducted whether or not the position of the ejected spot was deviated 0.2 mm or more from the initial, designed position.
(6) After the successful spots were formed on 40 pieces of the trays including 800 pieces of carriers, step (D) was conducted. Specifically, a successful spot to be formed originally was formed on the successful microarray at the position of the defective spot where no spot is formed in step (B), thereby providing a finished microarray including the successful spots aligned on the carriers in a predetermined pattern. In other words, the successful spots were formed in the positions where no spots were formed in the aforementioned procedures (3), (4) and (5). The successful spots were formed on the trays in the reverse order of Nos. 40, 39, 38 . . . 1.

Comparative Example 2

The microarray of COMPARATIVE EXAMPLE 2 was produced using the following procedures (1) to (10) under the following condition (B).

[Procedures (1) to (10)]
(1) A magnification camera was used to determine the presence or absence of the spots discharged from the discharge head, and the failure or no failure in the discharged direction (no failure was within ±3 degree in the vertical direction). After the determination, the defective discharge unit was tried to improve by adjusting the driving signal transmitted to the piezoelectric/electrostrictive element. Specifically, the driving signal was adjusted by changing the voltage value, the rise time to the predetermined voltage value, the time for keeping the predetermined voltage value, the voltage falling time and the like.
(2) When the aforementioned procedure (1) was not succeeded, the liquid sample was drawn out from the discharge unit of interest, i.e., by inserting a pipette or the like into the inlet to aspirate the liquid sample. Then, the liquid sample was again injected to inspect the discharged drops.
(3) The procedures (1) and (2) were repeated until all discharged drops were discharged from all discharge holes with certainty.
(4) Using all successful discharge units, successful sample spots were formed on 20 pieces of the carrier held on the tray No. 1 to provide a successful microarray on which the successful spots were aligned in a predetermined pattern on the carriers.

(5) Before proceeding with the next tray, the carrier on the tray formed immediately before was drawn out to inspect the spots. If the spots were defective, the driving signal transmitted to the piezoelectric/electrostrictive element of the discharge unit of interest was readjusted.

(6) If it was not succeeded by readjusting the driving signal, the liquid sample was drawn out from the discharge unit of interest by inserting the pipette or the like from the inlet of the discharge unit, and injecting again the liquid sample to inspect the spots.

(7) The procedures (5) and (6) were repeated until all discharged drops were discharged from all discharge holes with certainty.

(8) Using all successful discharge units, successful sample spots were formed on 20 pieces of the carrier held on the tray No. 2 to provide a successful microarray on which the successful spots were aligned in a predetermined pattern on the carriers.

(9) The procedures (5), (6), (7) and (8) were conducted to 40 pieces of the trays in the order of Nos. 1, 2, 3 . . . 40.

(10) The remaining 9 heads containing 960 types of c-DNAs were subjected to the aforementioned procedures (1) to (9). Using 960 types of c-DNAs in total, the successful spots were formed on 40 pieces of the trays including 800 pieces of the carriers. Thus, there was provided a finished microarray where the successful spots were aligned on the carrier in a predetermined pattern.

(Evaluation) After all spots were formed, the microarrays of EXAMPLES 3, 4 and 5 and COMPARATIVE EXAMPLE 2 were humidified by cooling to −20° C., and allowing them to stand at 22.5° C. and at humidity of 26%, baked at 80° C. for 1 hour, blocked by cleaning them with sterile purified water 3 times, immersing them into boiled water for 3 minutes and then into ethanol for 1 minute and hybridizing with fluorescent c-DNA to evaluate the spots. Specifically, the quality of the spots was determined by the number of ring failures having significantly different fluorescent values between the perimeter and the center. In this evaluation, the ring failure was defined as 10/1 or more fluorescent ratio of the perimeter to the center. A position accuracy of the spots were evaluated by measuring the displacement from the design positions using a microscope. When the spot was displaced ⅓ (40 μm) or more from the designed spot diameter, such a spot was defective.

(Results) The evaluation results are shown in Table 2.

TABLE 2

|  | Number of spots formation stopped in procedures (1) to (13) (average number per head) | Process time (hrs) | Number of defective rings (average number of 800 carriers) | Number of displaced spots (average number of 800 carriers) |
| --- | --- | --- | --- | --- |
| EX. 3 | 3 | 40 | 2 | 7 |
| Ex. 4 | 3 | 35 | 1.5 | 7 |
| Ex. 5 | 8 | 45 | 5.5 | 5 |
| COMP. EX. 2 | (Note 2) | 100 | 200 | 30 |

(Note 2):
The signal adjustment and the unit exchange were repeated until the stop of forming the spots were ended.

In EXAMPLE 4, it required 3 times greater amount of the cleaner, and 5 times longer time than normal for cleaning after the formation of the spots was stopped.

The results show that EXAMPLES 3, 4 and 5 are effective for the decrease in the process time, the decrease in the ring failures and the increase in the position accuracy. They work particularly well for the decrease in the ring failures. EXAMPLES 3 and 4, which are the second aspect of the present invention, have shorter process time and smaller numbers of ring failures than EXAMPLE 5, which is the first aspect of the present invention, since the inspection was per tray in EXAMPLE 5. Instead, EXAMPLE 5 has smaller numbers of displaced spots than EXAMPLES 3 and 4.

INDUSTRIAL APPLICABILITY

The method of producing the microarray according to the present invention is suitable for use in study, drug discovery, diagnosis, medical treatment, for example in analysis of the gene structure, detection of gene expression, study of gene function, pharmaco geonmics.

The invention claimed is:

1. A method of producing a microarray including sample spots on a carrier in a predetermined pattern by providing a plurality of discharge units each including a substrate having an inlet, a channel, a reservoir, and an outlet of a liquid sample, and a piezoelectric/electrostrictive element disposed at a position corresponding to the reservoir on the substrate; and by ejecting a liquid sample discharged from the outlet to outside onto the carrier to form the sample spots corresponding to each discharge unit on the carrier, the method comprising the steps of:

(A) ejecting the liquid sample discharged from the outlet to outside onto an inspection carrier to form inspection spots, inspecting the resultant inspection spots for their quality to determine whether the inspected spots are defective or successful, and detecting a defective discharge unit;

(B) making the detected defective discharge unit stop discharging the liquid sample from the outlet to outside, to prevent the formation of a defective sample spot from the defective discharge unit;

(C) forming successful sample spots on the carrier using successful discharge units to provide a successful microarray on which the successful spots are aligned in a predetermined pattern on the carrier; and (D) forming a successful spot to be formed originally on the successful microarray at the position of the defective spot where no spot is formed in step (B), thereby providing a finished microarray including the successful spots aligned on the carrier in a predetermined pattern, wherein the distance between the inspection carrier and the outlet when the inspection spots are formed in step (A) is set to be greater than the distance between the carrier and the outlet when the successful spots are formed in step (C).

2. A method of producing a microarray according to claim 1, wherein a series of steps (A), (B) and (C) is repeated a plurality of times, and then step (D) is conducted.

3. A method of producing a microarray according to claim 2, wherein when a plurality of successful microarrays are formed, the successful spot to be formed originally is formed in step (D) in a reverse order in step (C) on the successful microarray at the position of the defective spot where no spot is formed in step (B).

4. A method of producing a microarray according to claim 1, wherein the formation of the defective spot is stopped in step (B) by completely drawing out the liquid sample injected into the defective discharge unit.

5. A method of producing a microarray according to claim 4, wherein the defective discharge unit is further cleaned after the liquid sample is drawn out.

6. A method of producing a microarray according to claim 1, wherein the formation of the defective spot is stopped in step (B) by stopping the transmittance of an electrical signal for driving the piezoelectric/electrostrictive element.

7. A microarray produced by using the method according to claim 1.

8. A method of producing a microarray including sample spots on a carrier in a predetermined pattern by providing a plurality of discharge units each including a substrate including an inlet, a channel, a reservoir, and an outlet of a liquid sample, and a piezoelectric/electrostrictive element disposed at a position corresponding to the reservoir on the substrate; and by ejecting a liquid sample discharged from the outlet to outside onto the carrier to form the sample spots corresponding to each discharge unit on the carrier, the method comprising the steps of:

(A) ejecting the liquid sample discharged from the outlet to outside onto an inspection carrier to form inspection spots, inspecting the resultant inspection spots for their quality to determine whether the inspected spots are defective or successful, and detecting a defective discharge unit;

(B) making the detected defective discharge unit stop discharging the liquid sample from the outlet to outside, to prevent the formation of the defective sample spots from the defective discharge unit;

(C) forming successful sample spots on the carrier using successful discharge units to provide a successful microarray on which the successful spots are aligned in a predetermined pattern on the carrier;

(D) inspecting the quality of the successful spot of the resultant successful microarray to detect a second defective discharge unit;

(E) making the detected second defective discharge unit stop discharging the liquid sample from the outlet to outside, to prevent formation of a second defective sample spot from the second defective discharge unit;

(F) forming second successful sample spots on the carrier using second successful discharge units to provide a second successful microarray on which the second successful spots are aligned in a predetermined pattern on the carrier; and (G) forming a successful spot and a second successful spot, both being formed originally on the second successful microarray at the position of the defective spot and the second defective spot where no spots are formed in steps (B) and (E), thereby providing a finished microarray including the successful spots and the second successful spots aligned on the carrier in a predetermined pattern.

9. A method of producing a microarray according to claim 8, wherein a series of steps (A), (B), (C), (D), (E) and (F) is repeated a plurality of times, and then step (G) is conducted.

10. A method of producing a microarray according to claim 8, wherein the quality of the successful spots on the resultant successful microarray is preferably inspected with image processing or human eye using a display means capable of displaying in a noticeable manner only the successful spots formed simultaneously in step (D), and is determined whether they are defective or successful, thereby to detect a second defective discharge unit.

11. A method of producing a microarray according to claim 8, wherein the formation of the defective spot and/or the second defective spot corresponding to the defective discharge unit and/or the second defective discharge unit is stopped in step (B) and/or (E) preferably by completely drawing out the liquid sample injected into the defective discharge unit and/or the second defective discharge unit.

12. A method of producing a microarray according to claim 11, wherein the defective discharge unit and/or the second defective discharge unit are further cleaned after the liquid sample is drawn out.

13. A method of producing a microarray according to claim 8, wherein the formation of the defective spot and/or the second defective spot corresponding to the defective discharge unit and/or the second defective discharge unit is stopped in step (B) and/or (E) by stopping the transmittance of an electrical signal for driving the piezoelectric/electrostrictive element.

14. A method of producing a microarray according to claim 8, wherein the distance between the inspection carrier and the outlet when the inspection spots are formed in step (A) be set to be greater than the distance between the carrier and the outlet when the first and/or second successful spots are formed in steps (C) and/or (F).

15. A method of producing a microarray according to claim 8, wherein a successful spot and a second successful spot, both to be formed originally, are formed on the second successful microarray in step (G) at the position of the defective spot where no spot was formed in steps (B) and/or (E) in the reverse order of step (F).

16. A microarray produced by using the method according to claim 8.

17. A method of producing a microarray including sample spots on a carrier in a predetermined pattern by providing a plurality of discharge units each including a substrate including an inlet, a channel, a reservoir, and an outlet of a liquid sample, and a piezoelectric/electrostrictive element disposed at a position corresponding to the reservoir on the substrate; and by ejecting a liquid sample discharged from the outlet to outside onto the carrier to form the sample spots corresponding to each discharge unit on the carrier, the method comprising the steps of:

(A) ejecting the liquid sample discharged from the outlet to outside onto an inspection carrier to form inspection spots, inspecting the resultant inspection spots for their quality to determine whether the inspected spots are defective or successful, and detecting a defective discharge unit;

(B) making the detected defective discharge unit stop discharging the liquid sample from the outlet to outside, to prevent the formation of the defective sample spot from the defective discharge unit;

(C) forming successful sample spot on the carrier using successful discharge units to provide a successful microarray on which the successful spots are aligned in a predetermined pattern on the carrier; and (D) forming a successful spot to be formed originally on the successful microarray at the position of the defective spot where no spot is formed in step (B), thereby providing a finished microarray including the successful spots aligned on the carrier in a predetermined pattern, wherein when a plurality of successful microarrays are formed, the successful spot to be formed originally is formed in step (D) in a reverse order in step (C) on the successful microarray at the position of the defective spot where no spot is formed in step (B).

* * * * *